United States Patent [19]

Dolak

[11] 4,147,704

[45] Apr. 3, 1979

[54] DERIVATIVES OF NOVOBIOCIN

[75] Inventor: Lester A. Dolak, Cooper Township, Kalamazoo County, Mich.

[73] Assignee: The Upjohn Company, Kalamazoo, Mich.

[21] Appl. No.: 878,117

[22] Filed: Feb. 15, 1978

Related U.S. Application Data

[62] Division of Ser. No. 793,822, May 5, 1977.

[51] Int. Cl.$^2$ ........................................... C07D 311/56
[52] U.S. Cl. ............................. 260/343.45; 542/417; 542/439; 542/441; 195/80 R; 536/13; 424/281; 424/180
[58] Field of Search .................. 260/343.45; 542/417, 542/439, 441

[56] References Cited

U.S. PATENT DOCUMENTS

| | | | |
|---|---|---|---|
| 2,966,484 | 12/1960 | Walton | 260/343.45 |
| 2,966,509 | 12/1960 | Stammer | 260/343.45 |
| 3,049,534 | 8/1962 | Wallick | 536/13 |
| 3,049,551 | 8/1962 | Walton | 260/343.45 |
| 3,175,944 | 3/1965 | Hoeksema | 424/181 |
| 3,652,536 | 3/1972 | Sebek et al. | 536/4 |
| 3,890,297 | 6/1975 | Dolak | 536/4 |

*Primary Examiner*—Natalie Trousof
*Assistant Examiner*—Jane T. Fan
*Attorney, Agent, or Firm*—Bruce Stein

[57] ABSTRACT

The present invention relates to processes for the chemical oxidation of novobiocin-type compounds (I) to their corresponding hydroxy derivative (II) or aldehyde (III) and formation of novobiocin derivatives from these oxidation products. The oxidation products and derivatives have antibacterial activity.

6 Claims, No Drawings

DERIVATIVES OF NOVOBIOCIN

This is a division, of application Ser. No. 793,822, filed May 5, 1977.

BACKGROUND OF THE INVENTION

Novobiocin is an antibiotic useful in the treatment of staphylococcal infections and in urinary tract infections caused by certain strains of Proteus. It shows no cross resistance with penicillin and is active against penicillin-resistant strains of *Staphylococcus aureus*. Novobiocin is produced through fermentation by streptomycetes. The methods for production, recovery and purification of novobiocin are described in U.S. Pat. No. 3,049,534.

Dihydronovobiocin is an antibiotic prepared by hydrogenating novobiocin according to the procedures disclosed in U.S. Pat. No. 3,175,944.

As with any antibiotic it is always highly advantageous to prepare derivatives or analogs since these often lead to new antibiotics with increased potency, fewer and less severe side effects, and/or a different spectrum of antibiotic activity. In 1972 U.S. Pat. No. 3,652,536 disclosed an enzymatic process for cleaving novobiocin to produce novenamine. U.S. Pat. No. 3,890,297 disclosed a selective process for N-acylation of novenamine which produces novobiocin analogs which have antibacterial activity.

The following patents disclose modifications of novobiocin: U.S. Pat. Nos. 2,925,411; 2,938,899; 2,945,064; 3,049,550; and 3,445,455; British Pat. Nos. 856,816 and 997,179; and German Pat. Nos. 1,088,982 and 1,076,144.

However none of the above relate to modification of the isopentenyl side chain on the benzamido ring. To my knowledge only the combined process of U.S. Pat. Nos. 3,652,536 and 3,890,297 disclosed a useful method for producing such analogs until the present invention.

Allylic oxidation with selenium dioxide is known. For a recent review see N. Rabjohn in Organic Reactions, Vol. 24, pp. 261–415 (1976). A set of rules ordering the susceptibility of carbon atoms in an olefin to oxidation by selenium dioxide were first given by A. Guillemonat in Ann. Chim., 11, 143 (1939). However, these rules are known to have exceptions as discussed by E. N. Trachtenberg (Oxidation, Techniques and Applications in Organic Synthesis, R. L. Augustine, Ed., Marcel Dekker, New York, 1969, Chapter 3) and V. T. Bhalero and H. Rapoport in J.A.C.S., 93, 4835 (1971). These exceptions and lack of appropriate examples in the literature preclude a priori predictability of the site of attack in an olefin such as that in the novobiocin-type compounds (I). The products could have been as follows:

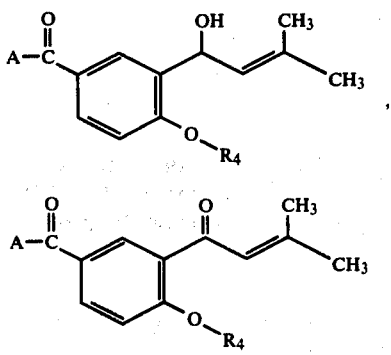

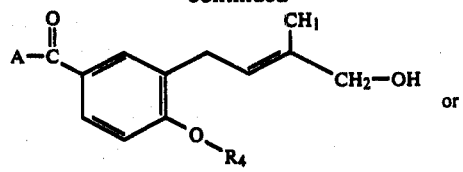

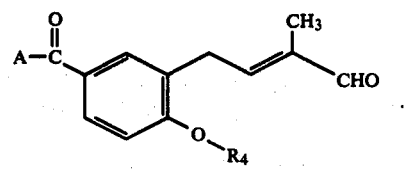

Since benzylic oxidation with selenium dioxide is known and since the above-cited rules state that methylene (—CH$_2$—) is oxidized prior to methyl (—CH$_3$) and since the methylene group in question is both benzylic and allylic it is surprising and unexpected that the reaction is completely regioselective. The only products observed were those resulting from attack at the trans methyl group.

SUMMARY OF THE INVENTION

Disclosed is an aldehyde novobiocin-type compound of the formula:

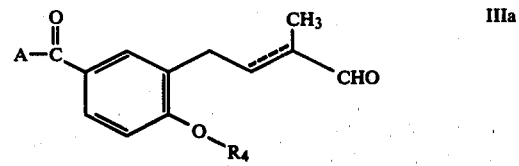

or pharmaceutically acceptable salt thereof.

Also disclosed is a hydroxynovobiocin-type compound of the formula:

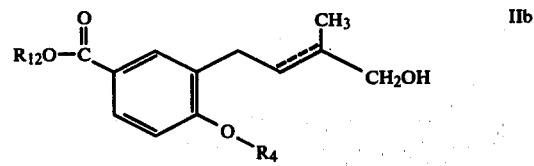

or pharmaceutically acceptable salt thereof.

Further disclosed is a compound of the formula:

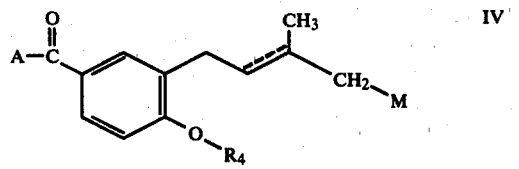

or pharmaceutically acceptable salt thereof.

Also disclosed is a compound of the formula:

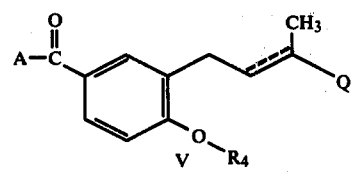

or pharmaceutically acceptable salt thereof.

Disclosed is a process for preparing an aldehyde novobiocin-type compound of the formula:

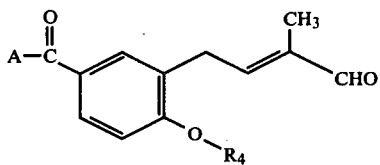

III which comprises (1) contacting a compound of the formula:

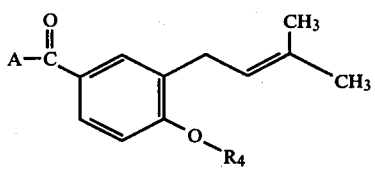

I with an oxidant and (2) recovering the aldehyde novobiocin-type compound (III).

Also disclosed is a process for preparing a hydroxynovobiocin-type compound of the formula:

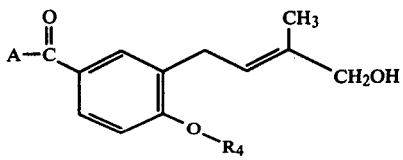

II which comprises (1) contacting a novobiocin-type compound (I) with an oxidant and (2) recovering the hydroxynovobiocin-type compound (II).

The definitions and explanations below are for the terms as used throughout the entire patent application including both the specification and claims.

Novobiocin, novenamine, novobiocic acid, ring A, ring B and ring C refer to particular chemical compounds as is well known to those skilled in the art. See, for example, U.S. Pat. Nos. 3,049,534; 3,652,536 and J.A.C.S. 79, 3789 (1957), etc.

However, as used in the present invention the terms novobiocin, novenamine, novobiocic acid, ring A, ring B and ring C refer to

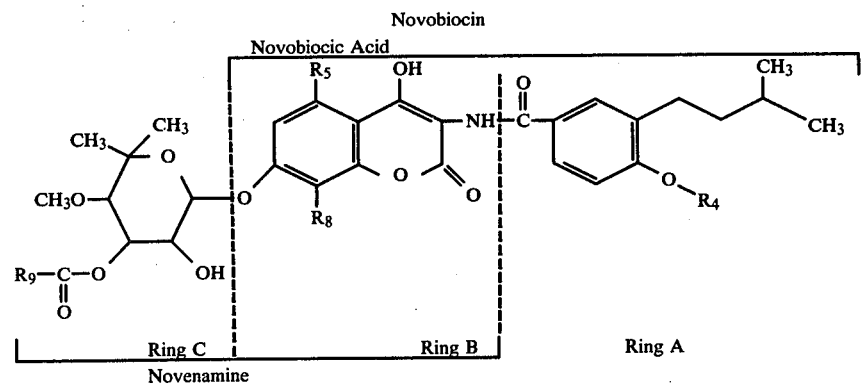

A is novenamine, ring B or —$OR_{12}$.
Novenamine is

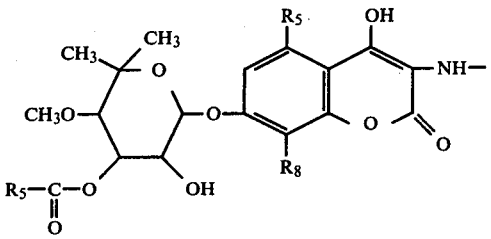

The lyxoside formula does not designate any particular stereochemical relationship.

$R_5$ and $R_6$ may be the same or different and are selected from the group consisting of hydrogen, alkyl of 1 thru 5 carbon atoms, halogen, nitro, cyano, carboxyl and —$NR_\alpha R_\beta$.

Halogen refers to fluorine, chlorine, bromine and iodine.

$R_\alpha$ and $R_\beta$ may be the same or different and are hydrogen or alkyl of 1 thru 5 carbon atoms.

$R_9$ is amino, 2-pyrryl, 2-(5-methyl)-pyrryl, 2-furyl and 2-(5-methyl)-furyl.

Ring B is

$R_{12}$ is alkyl of 1 thru 5 carbon atoms.
═ is a single or double bond.
$R_4$ is hydrogen or $$-\overset{O}{\underset{\|}{C}}-R_{12}$$

with the proviso that $R_4$ is hydrogen when A is novenamine or ring B.

M is halogen, —$N_3$, —$SR_{12}$, —$OR_{12}$, —$NR_\alpha R_\beta$, —$R_{12}$, or

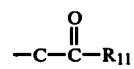

$R_{11}$ is —$OR_{12}$, alkyl of 1 thru 5 carbon atoms, phenyl, phenyl substituted in the para position with halogen, or alkyl of 1 thru 5 carbon atoms or —$OR_{12}$.

Q is selected from the group consisting of —CH=N—OH, —C≡N, —CH$_2$NH$_2$, —CHOH—R$_{11}$, —CO—R$_{11}$, —CH=N—NHR$_{10}$, —CO$_2$H, —CO$_2$—R$_{12}$, —CH=CH$_2$, R$_{12}$ or —CO—NH$_2$.

R$_{10}$ is hydrogen, phenyl or —CO—NH$_2$.

All temperatures are in degrees Centigrade.

TLC refers to thin layer chromatography.

THF refers to tetrahydrofuran.

DMSO refers to dimethylsulfoxide.

DMF refers to dimethylformamide.

PMR refers to proton magnetic resonance spectroscopy.

CMR refers to carbon magnetic resonance spectroscopy.

IR refers to infrared spectroscopy.

UV refers to ultraviolet spectroscopy.

Pharmaceutically acceptable refers to those properties and/or substances which are acceptable to the patient from a pharmacological-toxicological point of view and to the manufacturing pharmaceutical chemist from a physical-chemical point of view regarding composition, formulation, stability, patient acceptance and bioavailability.

When solvent pairs are used, the ratio of solvents used are volume/volume (v/v).

The present invention is a process for oxidation of a novobiocin-type compound (I) to a hydroxynovobiocin-type compound (II) and an aldehyde novobiocin-type compound (III). The hydroxynovobiocin-type compounds (IIb) within the scope of the compounds of formula (II) are novel as well as are the aldehyde novobiocin-type compounds (III).

The hydroxynovobiocin-type compounds (II) and aldehyde novobiocin-type compounds (II) produced by oxidation may have the double bond in the isopentenyl side chain reduced by hydrogenation as is well known to those skilled in the art forming the corresponding reduced compounds which are within the scope of the compounds of the formulas IIa and IIIa.

By known chemical reactions the hydroxynovobiocin-type compounds (IIa) can be transformed into novel derivatives (IV). Likewise, the aldehyde novobiocin-type compounds (IIIa) can be transformed into novel derivatives (V) by known chemical reactions. The novobiocin derivatives (IV and V) are useful as antibacterials in the same way as are novobiocin, dihydronovobiocin and chlorobiocin.

DETAILED DESCRIPTION OF THE INVENTION

The process of present invention oxidizes the trans-methyl group of the 3-methyl-2-butenyl side chain of novobiocin-type compounds (I)

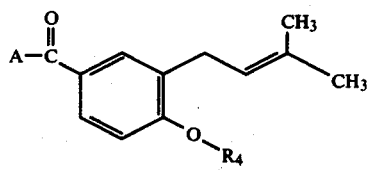

to the corresponding hydroxynovobiocin-type compound (II)

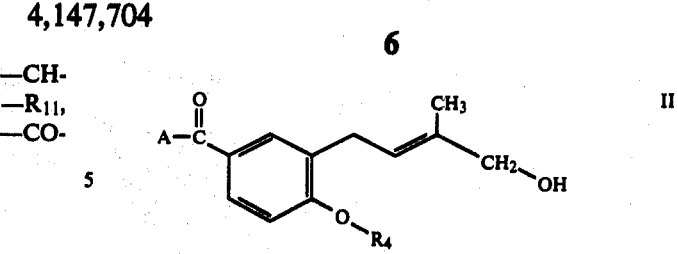

or the corresponding aldehyde novobiocin-type compound (III)

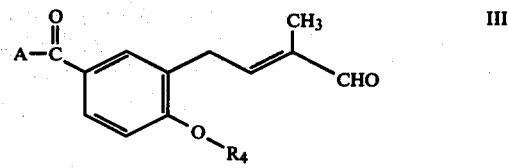

by contacting the novobiocin-type compound (I) with an oxidant.

The present invention may be more fully understood by reference to Chart A.

CHART A

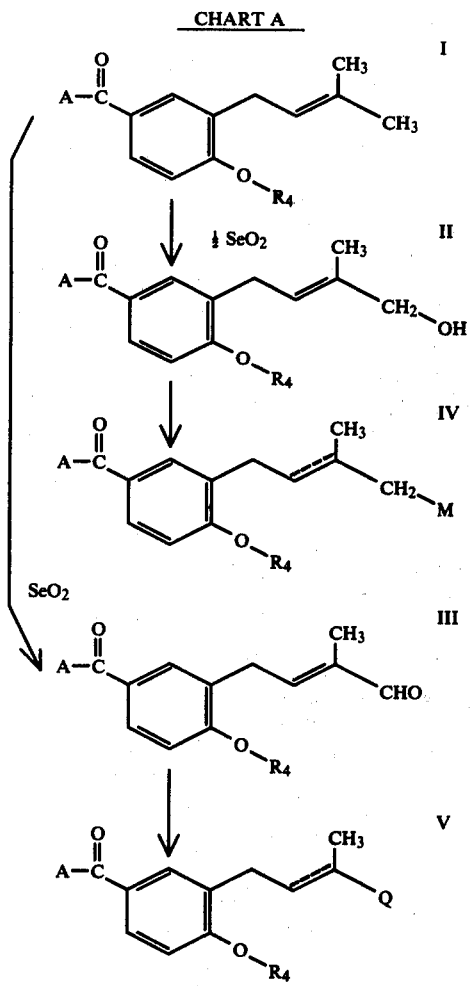

The compounds within the scope of formula I are either known to those skilled in the art or can be readily prepared from known compounds by methods well known to those skilled in the art. For example, novobiocin, dihydronovobiocin and chlorobiocin are well-known compounds. See U.S. Pat. Nos. 3,049,534;

3,175,944 and 3,682,886 respectively. Novobiocic acid is known, see J.A.C.S. 79, 3789 (1957).

Novobiocin-type compounds (I) may be prepared by reacting ring A with novenamine according to the procedure of U.S. Pat. No. 3,890,297. Likewise, novobiocic acid may be reacted with ring C to form novobiocin-type compounds (I).

Various oxidants are within the scope of the present invention. They are selenium dioxide, oxygen followed by reduction with agents such as dithionate or lithium aluminum hydride, lead tetraacetate followed by chemical or enzymatic hydrolysis, chromium trioxide, sodium or potassium dichromate ($Na_2Cr_2O_7$, $K_2Cr_2O_7$). It is preferred that the oxidant be selenium dioxide.

The amount of oxidant present will determine whether the hydroxynovobiocin-type compound (II) or the aldehyde novobiocin-type compound (III) is obtained. If the amount of the oxidant is less than one molar equivalent, preferably 0.1–0.8 equivalents, more preferably 0.3–0.7 equivalents the majority of the product formed will be the hydroxynovobiocin-type compound (II). If the amount of oxidant used is greater than one molar equivalent, preferably 1–5 molar equivalents, more preferably 1–3 molar equivalents the majority of the product formed will be the aldehyde novobiocin-type compound (III). It is understood that in producing either the hydroxy (II) or the aldehyde (III) novobiocin-type compounds a small amount of the other compound will usually be present. The hydroxy (II) and aldehyde (III) novobiocin-type compounds are easily separated from each other by methods well known to those skilled in the art.

When the oxidant is selenium dioxide and one wishes to make the aldehyde novobiocin-type compound (III) the novobiocin-type compound (I) and the selenium dioxide (greater than one molar equivalent) are refluxed in an organic diluent such as 95% ethanol, 100% ethanol, methanol, acetic acid, acetic anhydride, acetone, chloroform, THF, dioxane and mixtures thereof. It is preferred that the organic diluent be 95% ethanol. The reaction proceeds adequately between 25°–100° and takes from 1–72 hours depending on the temperature. It is preferable to perform the reaction under refluxing conditions so as to keep the reaction times relatively short. With refluxing ethanol the reaction is complete in about 3 hours.

When the hydroxynovobiocin-type compound (II) is the preferred product it is best to slowly (30 min.-1 hour) add the selenium dioxide in an organic diluent to the novobiocin-type compound (I) in an organic diluent under refluxing conditions. Under these conditions the reaction is complete in about 0.5–3 hours.

The reactions are worked up by methods well known to those skilled in the art. The mixture is filtered and concentrated by heating with reduced pressure. The concentrate is chromatographed on a column (silica gel or alumina) of appropriate size. Elution is performed with organic diluents usually used for such purposes and mixtures thereof such as ethyl acetate:methanol, 20:1 or chloroform:methanol, 19:1 for a silica gel column. Fractions of appropriate size are collected in the usual manner. Homogenous fractions (TLC) of a more polar compound than the starting material (I) are pooled and concentrated to give pure product.

The products are identified in the usual manner by IR, UV, PMR and CMR.

The hydroxynovobiocin-type compounds (IIa) and the aldehyde novobiocin-type compounds (IIIa) are useful as anti-bacterial agents in the same manner and in the same way as novobiocin, dihydronovobiocin and chlorobiocin. See U.S. Pat. Nos. 3,049,534, 3,175,944, and 3,682,886 except that concentrations used should be increased about 10 fold.

The aldehyde group on the 3-methyl-2-butenyl-4-hydroxy benzoic acid portion (Ring A) can be reacted by known chemical reactions to produce novel and useful novobiocin derivatives (V). For example, the aldehyde novobiocin-type compound (IIIa) can be reacted with (a) hydroxylamine to form an oxime (V), the oxime may be converted to the corresponding nitrile (V) or reduced with for example sodium borohydride to the corresponding primary amine (V); (b) a Grignard reagent to form a secondary alcohol (V) which may be oxidized to the corresponding ketone (V); (c) phenylhydrazine to form a phenylhydrazone (V); (d) hydrazine to form a hydrazone (V); (e) semicarbazide to form a semicarbazone (V), see Example 3; (f) manganese dioxide to form an acid (V) which can be reacted with an alcohol to form an ester (V); a Wittig reagent to form an alkene (V) which can be hydrogenated to the corresponding alkane (V).

Likewise, the primary alcohol group on the 3-methyl-2-butenyl-4-hydroxy benzoic acid portion (ring A) can be reacted by known chemical reactions to produce novel and useful novobiocin derivatives (IV). For example, the hydroxynovobiocin-type compounds (IIa) can be reacted with (a) tosyl chloride forming a tosylated intermediate which upon reaction with a nucleophile such as a halogen (chloride, bromide, etc.), alkoxide, azide (Example 4) or thioalkoxide forms the corresponding product (IV); or (b) a compound of the formula $R_{11}COCl$ where $R_{11}$ is previously defined.

The novobiocin derivatives (IV and V) are useful in the same manner and in the same way as are novobiocin, dihydronovobiocin, and chlorobiocin. In addition, the novobiocin derivatives (IV and V) can be used to sterilize glassware and utensils in the concentration range of 0.01–10.0%. Walls, bench tops and floors may be cleaned of susceptible organisms using the same concentration range. In addition the novobiocin derivatives (IV and V) may be used to selectively destroy susceptible organisms in soil samples prior to screening for antibiotics. Further, the novobiocin derivative (IV and V) may be used to destroy susceptible organisms in the bowels of animals for studies of digestion and excretion.

EXAMPLES

The invention may be more fully understood from the following examples which are illustrative of the process and compounds of the present invention but are not to be construed as limiting.

EXAMPLE 1

Oxidation of novobiocin (I) to novobiocin aldehyde (III) by selenium dioxide (See Chart A, Formulas I and III: $R_4$ is hydrogen, and A is novenamine)

Novobiocin (U.S. Pat. No. 3,049,534, 20.0 g.) is refluxed in ethanol (95%, 200 ml.) with selenium dioxide (10.0 g.) for 3 hours. The reaction is cooled to 25° and filtered. The filtrate is concentrated, ethyl acetate:methanol (100 ml., 20:1) is added and the mixture filtered. The filtrate is placed on a silica gel (230–400 mesh) column (15 × 150 cm.) and eluted with ethyl acetate:methanol, 20:1. Fractions containing the product (III) are pooled, concentrated and re-chromatographed on a silica gel (230-400 mesh) column (2.5 × 100 cm.) eluting with chloroform:methanol, 19:1 at 5 ml./min. flow rate. The fractions are assayed by TLC, and those containing homogenous material are pooled and concentrated to give novobiocin aldehyde (III).

EXAMPLE 2

Oxidation of novobiocin (I) to hydroxynovobiocin (II) by selenium dioxide (See Chart A, Formulas I and II: $R_4$ is hydrogen and A is novenamine)

Novobiocin (6.1 g.) is refluxed in ethanol (95%, 100 ml.). Selenium dioxide (0.5 g.) in ethanol (95%, 100 ml.) is added over a period of 45 min. to the refluxing novobiocin, after which the mixture is refluxed (1 hour), filtered while hot and the filtrate concentrated to a solid. The solid is dissolved in chloroform:methanol (20 ml., 1:1) and put on a silica gel (230-400 mesh) column (2.5 × 100 cm.). Elution is performed with chloroform:methanol, 1:1 at 4 ml./min. collecting 25 ml. fractions. Homogenous fractions (TLC) are pooled and concentrated to give hydroxynovobiocin (II).

EXAMPLE 3

Transformation of novobiocin aldehyde (IIIa) to the corresponding semicarbazone (V) (See Chart A, Formulas III and V: $R_4$ is hydrogen, ═ is a double bond and A is novenamine, Q is

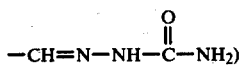

Novobiocin aldehyde (Example 1, 624 mg.) is dissolved in THF or dioxane (50 ml.). Semicarbazide hydrochloride (130 mg.) in water (5 ml.) and sodium acetate (200 mg.) are added and the mixture is stirred at 20°-100° for 1-72 hours. The reaction is monitored by TLC on silica gel using ethyl acetate:methanol, 10:1. When the reaction is complete as measured by TLC the mixture is filtered and the filtrate concentrated with heat under reduced pressure. The concentrated filtrate is partitioned between ethyl acetate and 0.05 N hydrochloric acid. The organic phase is washed with water, dried over magnesium sulfate, filtered, and concentrated under vacuum. The concentrate is dissolved in a small amount of the ethyl acetate:methanol mixture as above, and placed on a silica gel column of appropriate size. This column is developed at 0.5-10 ml./min. with the same organic diluent system. Fractions of 15 ml. each collected and homogenous fractions (TLC) which correspond to the product are pooled and concentrated to dryness. The residue is crystallized using a suitable solvent pair such as methanol:water to yield the semicarbazone (V).

EXAMPLE 4

Transformation of hydroxynovobiocin (IIa) to the corresponding azide (IV) (See Chart A, Formulas II and IV: $R_4$ is hydrogen, ═ is a double bond, A is novenamine and M is $-N_3$)

Hydroxynovobiocin (Example 2, 626 mg.) is dissolved in dry pyridine and a co-solvent such as THF or dioxane. The mixture is flushed with nitrogen and evacuated several times to remove oxygen. The mixture is cooled to $-10°$ to $10°$. A solution of tosyl chloride (210 mg.) in the corresponding co-solvent or as a dry powder is added at such a rate that the temperature does not rise above 10°. The reaction is monitored by TLC with the disappearance of the starting material and concomitant build up of product. When the reaction is complete (2-16 hours) the cold reaction mixture is poured into sufficient 0.1-1.0 N hydrochloric acid and ice to ensure neutralization of all the pyridine and no rise in temperature. The product is extracted into ethyl acetate. The organic phase is washed with water, dried over magnesium sulfate, filtered, and concentrated with heat under reduced pressure. The concentrate is taken up in a minimum amount (2-5 ml.) of ethyl acetate:methanol, 10:1 and placed on a silica gel (230-400 mesh) column (2.5 × 100 cm.). The column is developed with the above-identified solvent at a flow rate of 1-10 ml./min. while collecting 25 ml. fractions. The fractions are assayed by TLC. Homogenous fractions (TLC) containing material corresponding to the desired product are pooled and concentrated. The structure of the TLC-homogeneous material is demonstrated by PMR in $d_6$-DMSO.

The product is dissolved in DMF (50 ml.) and the mixture flushed with nitrogen. Sodium azide (1 g.) is added and the mixture stirred at 10°-100° for 1-72 hours. The reaction is monitored by TLC as described above. When the starting tosylate is no longer detected or when no additional azide (IV) is formed the reaction mixture is filtered and concentrated with heat under reduced pressure. The concentrate is dissolved and chromatographed as described above for the tosylate. The azide (V) is purified by crystallization from a suitable solvent pair such as acetone-water. The crystals are characterized by elemental analysis IR, UV, PMR and CMR.

I claim:

1. An aldehyde novobiocin-type compound of the formula:

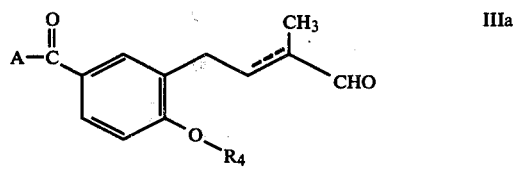

or a pharmaceutically acceptable salt thereof where A is ring B

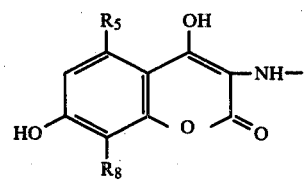

where $R_5$ and $R_8$ may be the same or different and are selected from the group consisting of hydrogen, alkyl of 1 thru 5 carbon atoms, halogen, nitro, cyano, carboxyl and $-NR_\alpha R_\beta$ where $R_\alpha$ and $R_\beta$ may be the same or different and are hydrogen or alkyl of 1 thru 5 carbon atoms; ═ is a single or double bond; and $R_4$ is hydrogen.

2. A compound according to claim 1 where $R_5$ is hydrogen, $R_8$ is methyl, and ═ is a double bond.

3. A compound of the formula:

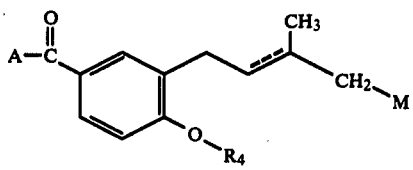

or pharmaceutically acceptable salt thereof where M is (1) halogen, $-N_3$, $-SR_{12}$, $-OR_{12}$, and $-NR_\alpha R_\beta$, where $R_{12}$ is alkyl of 1 thru 5 carbon atoms; and (2) $-R_{12}$,

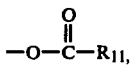

where $R_{11}$ is $-OR_{12}$, alkyl 1 thru 5 carbon atoms, phenyl, phenyl substituted in the para position with halogen, alkyl of 1 thru 5 carbon atoms, or $-OR_{12}$; where $-NR_\alpha R_\beta$, A, $R_4$ and≡are defined in claim 1.

4. A compound according to claim 3 where $R_5$ is hydrogen, $R_8$ is methyl, and≡is a double bond.

5. A compound of the formula:

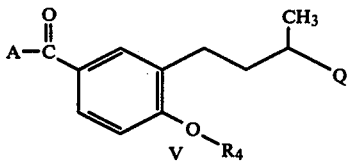

or pharmaceutically acceptable salt thereof where Q is selected from the group consisting of

—$CH_2$—$NH_2$

—CHOH—$R_{11}$

—CO—$R_{11}$

—CH=N—$NHR_{10}$

—$CO_2H$

—$CO_2$—$R_{12}$

—CH=$CH_2$

—$R_{12}$

—CO—$NH_2$ where $R_{10}$ is hydrogen, phenyl or —CO—$NH_2$; where $R_{11}$ and $R_{12}$ are defined in claim 3, and where $R_4$ is hydrogen; A is ring B

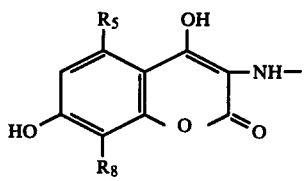

where $R_5$ and $R_8$ may be the same or different and are selected from the group consisting of hydrogen, alkyl of 1 thru 5 carbon atoms, halogen, nitro, cyano, carboxyl and —$NR_\alpha R_\beta$ where $R_\alpha$ and $R_\beta$ may be the same or different and are hydrogen or alkyl of 1 thru 5 carbon atoms; and≡is a single or double bond.

6. A compound according to claim 5 where $R_5$ is hydrogen, $R_8$ is methyl, and≡is a double bond.

* * * * *